(12) United States Patent
Eckmiller et al.

(10) Patent No.: US 7,177,697 B2  
(45) Date of Patent: Feb. 13, 2007

(54) MICROCONTACT STRUCTURE FOR IMPLANTATION IN A MAMMAL, ESPECIALLY A HUMAN BEING

(75) Inventors: Rolf Eckmiller, Neuss (DE); Steffen Suchert, Nürnberg (DE)

(73) Assignee: Intelligent Acquisition LLC, Brookfield, WI (US)

( * ) Notice: Subject to any disclaimer, the term of this patent is extended or adjusted under 35 U.S.C. 154(b) by 364 days.

(21) Appl. No.: 10/476,239

(22) PCT Filed: Apr. 30, 2001

(86) PCT No.: PCT/EP01/04865

§ 371 (c)(1), (2), (4) Date: Nov. 19, 2003

(87) PCT Pub. No.: WO02/087687

PCT Pub. Date: Nov. 7, 2002

(65) Prior Publication Data

US 2004/0172099 A1 Sep. 2, 2004

(30) Foreign Application Priority Data

Apr. 28, 2001 (DE) ............................... 101 20 908

(51) Int. Cl.  
*A61N 1/05* (2006.01)

(52) U.S. Cl. ...................................................... 607/54

(58) Field of Classification Search ................... 607/2, 607/53, 54, 141, 115, 116  
See application file for complete search history.

(56) References Cited

U.S. PATENT DOCUMENTS

| 4,628,933 | A | | 12/1986 | Michelson | |
|---|---|---|---|---|---|
| 5,109,844 | A | * | 5/1992 | de Juan et al. | 607/53 |
| 5,215,088 | A | | 6/1993 | Normann et al. | |
| 5,411,540 | A | * | 5/1995 | Edell et al. | 607/53 |
| 5,873,901 | A | * | 2/1999 | Wu et al. | 607/54 |
| 5,935,155 | A | * | 8/1999 | Humayun et al. | 607/54 |
| 6,230,057 | B1 | * | 5/2001 | Chow et al. | 607/54 |
| 6,324,429 | B1 | * | 11/2001 | Shire et al. | 607/54 |
| 6,400,989 | B1 | * | 6/2002 | Eckmiller | 607/54 |

FOREIGN PATENT DOCUMENTS

DE 19705987 5/1998

(Continued)

OTHER PUBLICATIONS

Article, "Hardware Architecture of a Neural Net Based Retina Implant for Patients Suffering from Retinitis Pigmentosa".

(Continued)

Primary Examiner—Scott M. Getzow  
(74) Attorney, Agent, or Firm—Robert W Becker & Associates; Robert W Becker

(57) ABSTRACT

The invention relates to a microcontact structure for epiretinal or cortical contacting of nerve tissue for a vision prosthesis in mammals or human beings. Due to the fact that the thickness of the surface of the microcontacts (2) is not constant along the surface of the microcontact structure, the resolution can be adapted to physiological requirements.

13 Claims, 1 Drawing Sheet

FOREIGN PATENT DOCUMENTS

| | | |
|---|---|---|
| DE | 10020846 | 12/2001 |
| EP | 0 460 320 | 12/1991 |
| WO | WO 96/39221 | 12/1996 |

OTHER PUBLICATIONS

Article, "Development of Flexible Stimulation Devices for a Retina Implant System".

Article, "Flexible, Polyimide-Based Neural Interfaces".

Article, "Biomedical Microdevices for Neural Interfaces".

Article, "Cross-Sectional Investigation of the Internal Interface Between Biological Cell Tissue and Implant Materials in the Transmission Electron Microscope".

Article, "Flexible Silicon Structures for a Retina Implant".

\* cited by examiner

MICROCONTACT STRUCTURE FOR IMPLANTATION IN A MAMMAL, ESPECIALLY A HUMAN BEING

BACKGROUND OF THE INVENTION

The present invention relates to a microcontact structure provided for implantation in a mammal, in particular in a human being, and for contacting nerve tissue in the visual system. More precisely, the microcontact structure is to be arranged for contacting the ganglion cells in the retina around the fovea, on the one hand, or for contacting the visual cortex (area VI).

Losses of sight triggered or acquired by a genetic defect may inter alia have two causes. The first cause is the destruction of the photoreceptor layer in the retina following which impacting photons are not converted into corresponding stimulation of the ganglion cells. In the case of these symptoms, the ganglion cells are only partially affected so an external stimulation of the ganglion cells still present can generate visual perception. For some time, developments have been carried out on this basis, comprising the implantation of a microcontact structure for contacting the ganglion cells.

The second important cause of loss of sight in the present context may lie in an interruption of these signal transmissions between the ganglion cells and the region in the brain responsible for visual perception or in faulty operation of the ganglion cells themselves. For these symptoms, implants are also being developed in which a microcontact structure is directly in contact with the visual cortex, more precisely area VI of the visual cortex, where it generates visual perception owing to electrical stimulation.

The previously known microcontact structures substantially consist of a carrier material carrying electrically conductive, pin-shaped or needle-shaped contact elements on one side which rise above the plane of the carrier film. Microcontact structures of this type are known, for example from U.S. Pat. Nos. 5,109,844, 5,159,927, 5,411,540, DE 19525570 A1 or EP 0460320 B1. In all these microcontact structures, the individual contacts are uniformly distributed, i.e. with a constant surface density, on the surface of the implant. The surface density is approximately in the range of up to 20 contacts per mm$^2$. It has previously been assumed here that a surface density of the microcontacts which is as high as possible is desirable to increase the visual resolution.

It has been shown in practice that this concept is just as problematical as the previously known microcontact structures. One problem is that with the increasing number of microcontacts there is a corresponding increase in the external arrangement feeding these microcontacts. Each individual microcontact is fed according to present concepts by a separate channel of an encoder. The boundary conditions of this external device are the dimensions, the energy consumption and finally also the costs. When a certain number of microcontacts can be fed by a given external supply unit, visual perception which is as optimum as possible should be produced with this number of microcontacts. The present distribution of microcontacts with constant surface density is disadvantageous for this as it does not take into account that a region of the central visual field should be evaluated more highly for the recognition of certain objects than the surrounding edge region.

Furthermore, the tissue to be contacted by the microcontacts is not constructed in such a way that a specific spacing of two points from one another on the tissue corresponds in every region of the visual field to the same angular spacing based on the visual axis. Rather, it is the case that in the case of the ganglion cells of the retina around the region of the sharpest vision, called the fovea, no ganglion cells at all are initially present, then at a slight radial spacing from the central point of the fovea there is a great density of ganglion cells which leads to a crater-like curvature at the edge of the fovea. The layer of ganglion cells becomes thinner adjacent to this region.

If this region is occupied by a microcontact structure having a constant surface density of the microcontacts, the microcontacts in the center of the fovea do not reach any ganglion cells. The channels of the external supply device connected to these microcontacts remain without a physiological function. Very many ganglion cells are present per surface unit in the region of the "crater edge" of the fovea, so for a given number of ganglion cells relatively few microcontacts are available. The surface density of the ganglion cells then decreases in the outer region, while the surface density of the microcontacts remains the same. The number of microcontacts available for a specific number of ganglion cells therefore increases.

These physiological facts lead to there being relatively few microcontacts available precisely in the region responsible for the central visual field and the region of sharpest vision, namely the "crater edge" of the fovea, while in the surrounding region which plays a relatively subordinate part in visual perception, there are a proportionally large number of microcontacts available. The result achieved with a microcontact structure of this type with constant surface density is therefore not optimum, either with respect to the visual impression achieved which under-represents the most important part of the visual field, or with respect to the most effective use possible of the external supply device.

The same is true for contacting the visual cortex. The association between the surface of corresponding visual field sites on the brain surface and the visual field depicted is not linear there either. A microcontact structure with a constant surface density of the microcontacts would also lead here to an under-representation of the central region of the visual field based on the physiological evaluation of the visual field.

It is therefore the object of the present invention to provide a microcontact structure which allows contacting of the nerve tissue while taking into account the non-linear association between tissue surface and the visual field and which also allows, in the case of a limited number of available channels to connect them with the tissue in such a way that the physiologically more highly valued part of the visual field is depicted with a greater number of microcontacts than the less valued part of the visual field.

SUMMARY OF THE INVENTION

This object is achieved for implantation in the eye by a microcontact structure, for implantation on the visual cortex by a microcontact structure, in that the surface density of the microcontacts is not constant over the surface of the microcontact structure.

Since the surface density of the microcontacts is not constant over the surface of the microcontact structure in the microcontact structure for implantation in the eye, the distribution of the microcontacts can be selected such that the available channels, which are limited by the external resources, are associated as efficiently as possible with the visual field to be depicted. In the process, regions of the visual field with a higher physiological evaluation receive a higher microcontact density than regions with lesser relevance. In addition, the surface density of the microcontacts can be adapted to the density of the neurons to be contacted in the respective contacted tissue.

It is advantageous here if a round or oval rotationally symmetrical configuration with a central point is selected in the microcontact structure for epiretinal contacting, the central point in the implanted state being arranged in the region of the fovea of the eye and a region with a radius of about 175 to 200 µm around this central point being free of microcontacts, at least of actively used microcontacts.

The microcontacts are preferably arranged with their greatest available surface density in a region radially spaced from the central point by about 200 µm to 1,200 µm. In a region radially spaced from the central point by more than about 1,200 µm and which is physiologically less valued, the microcontacts preferably have a lower surface density than in the first region, so less resources of the external supply device are required for this region.

The microcontacts are preferably arranged substantially rotationally symmetrically around the central point of the microcontact structure.

The distribution of the microcontacts in the first region and in the second region is advantageously continuously varied, a surface density maximum being located in the first region and the surface density continuously decreasing radially outwardly from there. In view of the limited number of microcontacts (a few hundred per implant) a virtually continuous distribution can also be referred to.

A further optimization is achieved between the physiological benefit of the visual perception produced by the microcontact structure and the number of available microcontacts or the resources connected to the microcontacts if the surface density of the microcontacts in the plane representing the horizontal in the natural visual field is greater than in the regions which are located at the top and bottom in the natural visual field.

The same is true for the microcontact structure for implantation on the visual cortex. The microcontacts are arranged there, preferably in a substantially parabolic region corresponding to the retinotopic projection of the visual field onto the visual cortex, more precisely onto the area VI per half visual field, the surface density of the microcontacts having a maximum in the region of the vertex of the parabola. Thus, the parabolic region preferably corresponds to the form of the visual cortex, the greatest density of microcontacts being in a region corresponding to the fovea. About 90% of the microcontacts are preferably arranged in the region which corresponds to a substantially concentric visual field with an angular aperture of 5° from the visual axis.

The surface density of the microcontacts, starting from the region associated with the fovea, preferably decreases continuously or virtually continuously in each direction. A particularly good use of the resources is thus achieved here if the surface density in the direction depicting the horizontal plane of the natural visual field is higher than in the regions which depict top and bottom in the natural visual field. With respect to the retinotopic projection, this means that the surface density of the microcontacts decreases along a line from the point corresponding to the fovea along the axis of symmetry of the parabola in the temporal and more eccentric direction.

BRIEF DESCRIPTION OF THE DRAWINGS

Two embodiments of the present invention will be described hereinafter with the aid of the drawing, in which.

DESCRIPTION OF PREFERRED EMBODIMENTS

Figure 1:
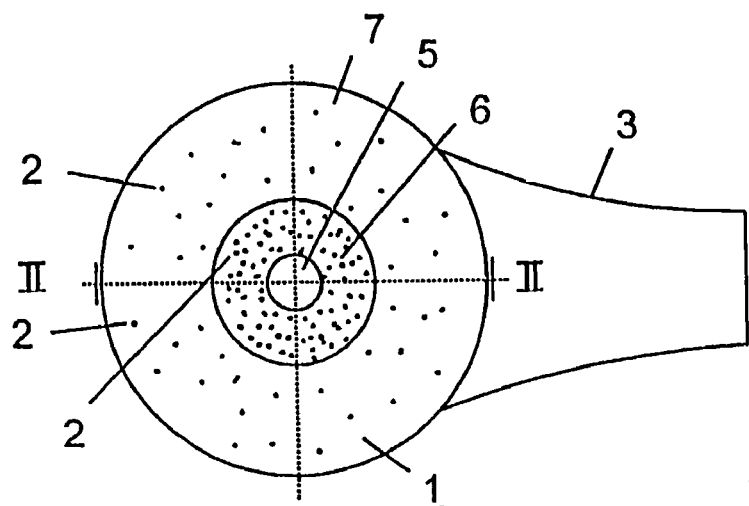
FIG. 1 shows a plan view of a microcontact structure with substantially rotationally symmetrical arrangement for epiretinal implantation.

FIG. 1 shows a plan view of a microcontact structure with a virtually rotationally symmetrical arrangement for epiretinal implantation in an eye.

The microcontact structure has a virtually circular carrier film 1 which is divided, for example, into a plurality of sectors and is made of polyamide. A large number (in FIG. 1 about 200) of microcontacts 2 is formed on this carrier film, the microcontacts 2 consisting in a manner known per se, for example of small precurved platinum structures standing substantially vertically on the carrier film. These microcontacts 2 are in turn connected via conductor tracks to a data line 3 leading outwards which conducts signals unidirectionally or bidirectionally to the microcontacts 2, or receives them. A wireless communication can also be provided instead of a data line.

The carrier film 1 has three concentric regions in total, a central region 5 which in the implanted state covers the fovea, a first region 6 which in the implanted state covers the crater-shaped edge of the fovea, and an outer region 7 which covers the regions of the retina radially situated further out.

In a concrete embodiment, the region 5 may also be free of material, in other words may form a central hole in the implant. This region 5 is without any function for the implant in the present context.

The first region 6 contacts the "crater edge", in other words the region immediately surrounding the fovea, in which the density of the ganglion cells is greatest. The region of the ganglion cells which corresponds to the central foveal and parafoveal visual field is also arranged here. The microcontacts 2 with the greatest surface density are therefore arranged in this region 6. Of the around 200 microcontacts in FIG. 1, the region 6 contains about 180. It represents a visual field up to an eccentricity of about 8° (conical with an angular aperture of 16°).

The region 6 will not be planar in a concrete embodiment, but adapted to the outer contour of the foveal region of the retina and optionally divided into sectors.

Figure 2:
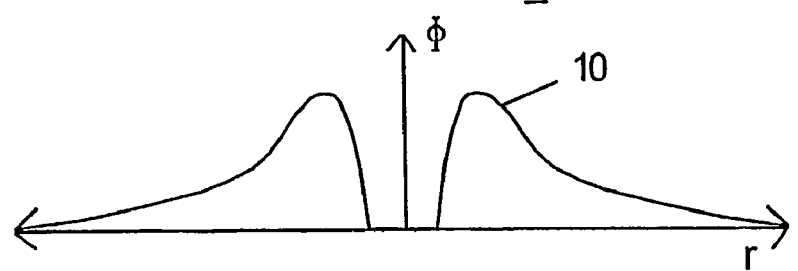
FIG. 2 shows a graphic view of the course of the surface density of the microcontacts in the radial direction.

FIG. 2 shows the idealized functional connection between the radial spacing of a point on the microcontact structure from its central point and the surface density $\Phi$ of the microcontacts. It can be seen that the central region 5 is free of microcontacts, therefore has the surface density 0. The first region 6 has a maximum at 10 which coincides as precisely as possible with the region of the highest ganglion cell density of the retina. The second outer region 7 finally has a decreasing surface density which also reflects the physiologically lesser significance of the associated outer visual field. In operation, the first region 6 with its higher resolution should allow the implant wearer to see an object, while the second region with its lower resolution should allow in particular perception of movement.

Figure 3:
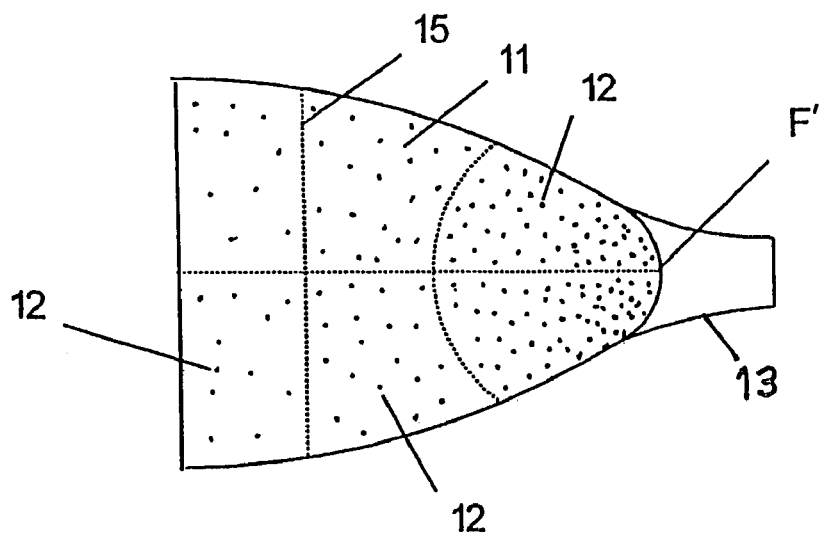
FIG. 3 shows a microcontact structure, also in plan view, with substantially parabolic arrangement for cortical implantation.

FIG. 3 shows a plan view of a cortical implant 11 with microcontacts 12 which are arranged perpendicularly to the plane of the carrier film on the surface as in the embodiment according to FIG. 1. A unidirectional or bidirectional data line 13 produces the connection to an external resource as in FIG. 1.

The form of the implant corresponds to the form of the right visual cortex in the brain of a Rhesus monkey, in that the visual field is depicted on a parabolic region. This retinotopic depiction of the visual field onto the area VI of the visual cortex is known from literature and proven experimentally, see Tootell et al., *J. Neur. Sci.* 1988, Vol. 8, page 1531 to 1568. Similarly, the visual field of other mammals is also depicted on the respective visual cortex, the form of which may be different.

In addition to the implant shown, contacting the right visual cortex, a second mirror-inverted implant is provided which contacts the opposing left visual cortex. Both half fields of vision are then accessible thereby.

Figure 4:
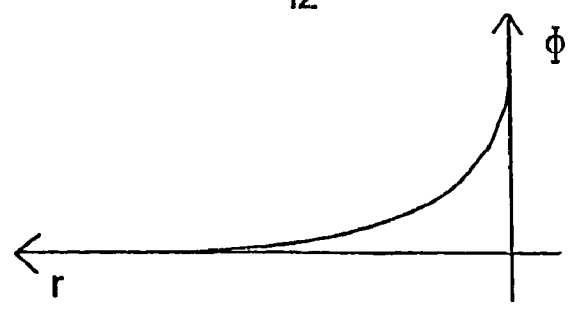
FIG. 4 shows a graphic view of the course of the surface density of the microcontacts in the direction of the axis of symmetry of the parabolic apparatus according to FIG. 3.

The surface density of the microcontacts is illustrated in FIG. 4 in a view corresponding to FIG. 2. Starting from the vertex of the parabola designated by F' and corresponding to the fovea of the retina, the surface density decreases continuously, a region extending from the point F' to about the line 15 representing a visual field up to an eccentricity of 5° for the associated left half visual field. This region contains around 80% of the available microcontacts 12.

For the implant wearer, this configuration means that, as described above, the central region allows the recognition of objects up to an eccentricity of, for example 5°, to be seen while the region of greater eccentricity located outside this cone only allows perception which possibly causes the implant wearer to turn to the peripherally perceived object in order to be able to see it.

In the case of a limited number of available stimulating channels in the external resource, from which one has to proceed in reality, an improved result with respect to perceiving and seeing objects and people is thus achieved with a non-uniform distribution of the microcontacts over the surface of the microcontact structure than is possible with the previously known microcontact structures with uniform surface density of the microcontacts.

Apart from the described distributions, other configurations are also possible, for example with an even greater concentration in the region of the fovea which possibly allows reading of texts, but with the given number of externally supplied channels only allows slight peripheral perception. In road traffic, a distribution with other main centers may be advantageous, emphasizing peripheral perception important to the pedestrian, to the disadvantage of a high resolution in the central visual field.

The microcontacts themselves may be designed pointed in design or have a particularly small diameter in regions with a greater surface density, while in the outer regions with a lower surface density of microcontacts they may have a blunter configuration, for example hemispherical. Thus, in the first regions the associated receptive fields are very selectively stimulated, while in the outer region greater receptive fields with few microcontacts are achieved.

While it was described in the embodiments that the number of microcontacts actually present varies per surface unit, in other embodiments microcontacts with a uniform surface density may also be present if the number of microcontacts actively connected with the external resource varies. A greater number of microcontacts may then be physically present in the peripheral region but not contacted, while in the region of the central visual field every or virtually every microcontact is active.

The specification incorporates by reference the disclosure of German priority document 101 20 908.8 Apr. 28, 2001 and PCT/EP01/04865 filed Apr. 30, 2001.

The present invention is, of course, in no way restricted to the specific disclosure of the specification and drawings, but also encompasses any modifications within the scope of the appended claims.

The invention claimed is:

1. A microcontact structure for epiretinal contacting of nerve tissue in an eye for a vision prosthesis in mammals or human beings, wherein a surface density of microcontacts is not constant over the surface of the microcontact structure, and wherein the surface density in a direction depicting a horizontal plane of the natural visual field is higher with the same eccentricity than in regions depicting top and bottom in the natural visual field.

2. A microcontact structure according to claim 1, wherein a central point is provided which, in an implanted state, is arranged in the region of the fovea of the eye, and wherein a region with a radius of about 175 μm to 200 μm is free of microcontacts around this central point.

3. A microcontact structure according to claim 2, wherein the microcontacts with the greatest surface density are arranged in a first region radially spaced from the central point by about 200 μm to 1,200 μm.

4. A microcontact structure according to claim 2, wherein the microcontacts are substantially rotationally symmetrically arranged around the central point of the microcontact structure.

5. A microcontact structure according to claim 3, wherein the microcontacts in a second region radially spaced from the central point by more than about 1,200 μm have a lower surface density than in the first region.

6. A microcontact structure according to claim 5, wherein the distribution of the microcontacts varies continuously in the radial direction in the first region and the second region, a surface density maximum being located in the first region and the surface density continuously decreasing radially outwardly from there.

7. A microcontact structure according to claim 1, wherein the microcontacts are arranged in a region substantially adapted to the retinotopic projection of a central visual field, the surface density of the microcontacts having a maximum in the region of projection of the fovea.

8. A microcontact structure according to claim 1, wherein the contacted region corresponds to the form of the visual cortex.

9. A microcontact structure according to claim 1, wherein the surface density of the microcontacts decreases continuously, starting from a region associated with the fovea, in a direction of increasing eccentricity.

10. A microcontact structure for contacting nerve tissue of the visual cortex for a vision prosthesis in mammals or human beings, wherein a surface density of microcontacts is not constant over the surface of the microcontact structure, and wherein the surface density in a direction depicting a horizontal plane of the natural visual field is higher with the same eccentricity than in regions depicting top and bottom in the natural visual field.

11. A microcontact structure according to claim 10, wherein the microcontacts are arranged in a region substantially adapted to the retinotopic projection of a central visual field, the surface density of the microcontacts having a maximum in the region of projection of the fovea.

12. A microcontact structure according to claim 10, wherein the contacted region corresponds to the form of the visual cortex.

13. A microcontact structure according to claim 10, wherein the surface density of the microcontacts decreases continuously, starting from a region associated with the fovea, in a direction of increasing eccentricity.

* * * * *